(12) United States Patent
Henning et al.

(10) Patent No.: US 12,156,862 B2
(45) Date of Patent: Dec. 3, 2024

(54) MEDICAMENTS FOR THE TREATMENT OF VASOCONSTRICTION RELATED DISEASES OR DISORDERS

(71) Applicant: Sulfateq B.V., Groningen (NL)

(72) Inventors: Robert Henk Henning, Groningen (NL); Gerrit Jan Willem Euverink, Haren (NL); Guido Krenning, Groningen (NL); Adrianus Cornelis Van der Graaf, Groningen (NL)

(73) Assignee: Sulfateq B.V., Groningen (NL)

( * ) Notice: Subject to any disclaimer, the term of this patent is extended or adjusted under 35 U.S.C. 154(b) by 174 days.

(21) Appl. No.: 16/640,785

(22) PCT Filed: Aug. 23, 2018

(86) PCT No.: PCT/EP2018/072735
§ 371 (c)(1),
(2) Date: Feb. 21, 2020

(87) PCT Pub. No.: WO2019/038361
PCT Pub. Date: Feb. 28, 2019

(65) Prior Publication Data
US 2021/0128523 A1    May 6, 2021

(30) Foreign Application Priority Data

Aug. 25, 2017  (NL) .................................. N2019446
May 24, 2018  (NL) .................................. N2020985

(51) Int. Cl.
*A61K 31/353*    (2006.01)

(52) U.S. Cl.
CPC .................. *A61K 31/353* (2013.01)

(58) Field of Classification Search
CPC .............. A61K 31/353; A61K 31/4025; A61K 31/496; A61K 31/5377; A61P 29/00; A61P 3/08; A61P 39/06; A61P 9/08; A61P 9/10; A61P 9/12
See application file for complete search history.

(56) References Cited

FOREIGN PATENT DOCUMENTS

| EP | 2935232 A1 | 10/2015 |
|---|---|---|
| WO | 20140098586 A1 | 6/2014 |
| WO | 20160188766 A1 | 12/2016 |

OTHER PUBLICATIONS

International Search Report for PCT/EP2018/072735 issued on Dec. 3, 2018.
International Preliminary Report on Patentability for PCT/EP2018/072735 issued on Mar. 5, 2020.
(Continued)

*Primary Examiner* — Savitha M Rao
(74) *Attorney, Agent, or Firm* — David Owen; Hoyng Rokh Monegier

(57) ABSTRACT

The present invention relates to medicaments for use in the prophylaxis or treatment of vasoconstriction related disorders or conditions. Specifically, the present invention relates to (2R) enantiomeric form of a 6-chromanol derivative for use in the prophylactic or treatment of vasoconstriction related disorders or conditions. A preferred 6-chromanol derivative is (6-hydroxy-2,5,7,8-tetramethylchroman-2-yl)(piperazin-1-yl)methanone; N-(benzyl)-6-hydroxy-2,5,7,8-tetramethylchroman-2-carboxamide; N-(phenyl)-6-hydroxy-2,5,7,8-tetramethylchroman-2-carboxamide; methyl 4-(6-hydroxy-2,5,7,8-tetramethylchroman-2-carboxamido)benzoate; (6-hydroxy-2,5,7,8-tetramethylchroman-2-yl)(morpholino)methanone, and pharmaceutically acceptable salts thereof.

10 Claims, 6 Drawing Sheets

(56) References Cited

OTHER PUBLICATIONS

Figure 1:
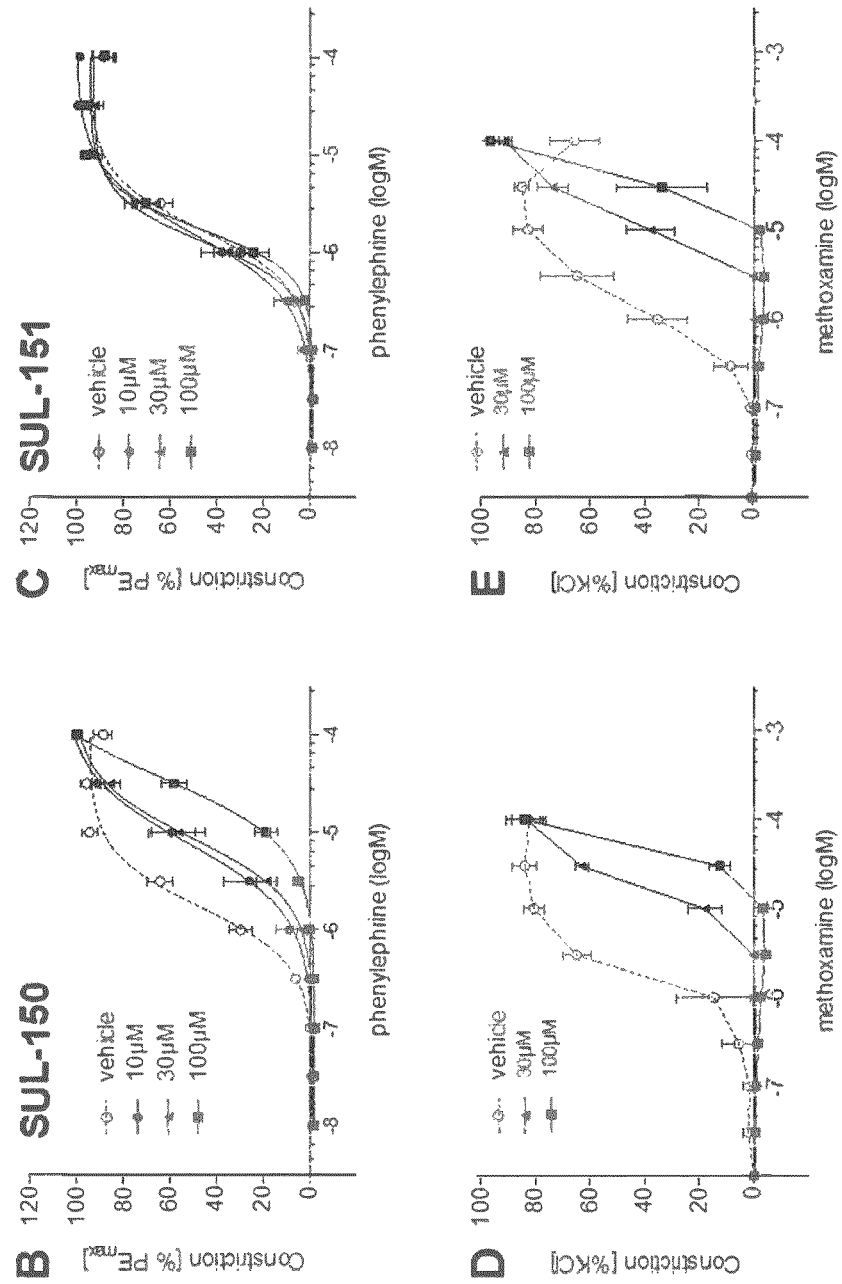

Bing Han et al: "The anti-inflammatory and bronchodilating properties of the novel pharmacological compound Sul-121", Internet Citation, Apr. 24, 2015, retrieved from the Internet: URL:http://www.nvfarmaco.nl/assets/docs/Abstracts_NVF_Voorjaarsdag_2015.pdf.

Bing Han et al: "The novel compound Sul-121 inhibits airway inflammation and hyperresponsiveness in experimental models of chronic obstructive pulmonary disease", Scientific Reports, vol. 6 No. 1, May 27, 2016

MEDICAMENTS FOR THE TREATMENT OF VASOCONSTRICTION RELATED DISEASES OR DISORDERS

CROSS-REFERENCE TO RELATED APPLICATIONS

This application is a U.S. National Stage under 35 USC 371 of PCT application PCT/EP2018/072735 filed on Aug. 23, 2018, which claims priority to Netherlands patent application 2019446, filed Aug. 25, 2017, and to Netherlands patent application 2020985, filed May 24, 2018. All the foregoing applications are hereby incorporated by reference in their entireties.

The present invention relates to medicaments for use in the prophylaxis or treatment of vasoconstriction related disorders or conditions.

Vasoconstriction related disorder comprise a group of disorders, like for example pulmonary hypertension, portal hypertension, vasospastic diseases, Raynaud's disease, acrocyanosis, livedo reticularis, post-traumatic dystrophy, occlusive diseases associated with inflammation and Buerger's disease.

Vasoconstriction is the process of constriction of blood vessels, which may result in decrease of flow of blood. Normal blood flow is necessary for carrying oxygenated blood to all parts of the body and when the normal flow is disrupted it may cause various problems. Vasoconstriction can occur due to medical condition or due to psychological disorder. This condition happens when the small muscles of the walls constrict causing narrowing of blood vessels. Actually this process is exactly opposite condition of vasodilation in which the blood vessels enlarge or open widely. The contraction of blood vessels can increase the heat of the body and may cause vascular conflict. Following this condition, the skin becomes paler than before since blood supply is drastically reduced. It occurs mostly on large arteries thus obstructing the blood flow but sometimes it can develop on small arterioles causing constriction of blood vessels.

An alpha adrenoreceptor antagonist (which is a vasodilator) can be administered for reducing the constriction of blood vessels and increasing blood flow. Treating the problem with calcium channel blockers would facilitate widening of blood vessels.

Control of hypertension in the vascular patient is clearly a priority. However, these patients often will have significant co-morbidities that may influence the choice of medication. The 5 main categories of drugs used in the initial treatment of hypertensive vascular diseases are (1). diuretics, (2). beta-adrenergic blockers, (3). calcium channel blockers, (4). angiotensin-converting enzyme (ACE) inhibitors, and (5). angiotensin receptor blockers (ARBs). Each of the antihypertensive agents is roughly equally effective, producing a good antihypertensive response in 40% to 60% of cases. Some antihypertensives, especially ACE and ARBs, also may have beneficial effects on the vascular and metabolic systems separate from their blood pressure lowering effects, which suggests they may be beneficial even if blood pressure is well maintained with other agents.

However, there remains a need for new compounds for treatment of vasoconstriction related disorders, in particular ones that have less side effects, or preferably no side effects at all in the dosing range of such compound.

It is an object of the present invention to provide compounds for the treatment of vasoconstriction related disorders or conditions.

The above object is met by the present invention by the (2R) enantiomeric form of certain 6-chromanol derivatives for use in the treatment of vasoconstriction related disorders or conditions.

Certain chromanol compounds have been described in e.g. WO2014/098586, WO2015/193365 and WO2016/188766. These compounds show a wide variety of protective effects on cells and organs. The compounds described in detail are developed by Sulfateq, and have abbreviations, referring to SUL-XXX (XXX being a 2 or 3 digit number). Many of these compounds are racemic mixtures, although some enantiomers have been tested as well.

Unexpectedly, upon further research, a number of the SUL compounds showed reversal effects of vascular constriction, which effect is useful in the treatment of vasoconstriction related disorders.

Thus, the present invention relates to the (2R) enantiomeric form of a 6-chromanol derivative wherein the 6-chromanol derivative is chosen from the group consisting of (6-hydroxy-2,5,7,8-tetramethylchroman-2-yl)(piperazin-1-yl)methanone (SUL-121); (6-hydroxy-2,5,7,8-tetramethylchroman-2-yl)(morpholino)methanone (SUL-95); N-(benzyl)-6-hydroxy-2,5,7,8-tetramethylchroman-2-carboxamide (SUL-96), N-(4-fluorobenzyl)-6-hydroxy-2,5,7,8-tetramethylchroman-2-carboxamide (SUL-97); 6-hydroxy-N—((S)-2-hydroxy-1-phenylethyl)-2,5,7,8-tetramethylchroman-2-carboxamide (SUL-98); N-(phenyl)-6-hydroxy-2,5,7,8-tetramethylchroman-2-carboxamide (SUL-103); 6-hydroxy-2,5,7,8-tetramethyl-N-(2-nitrophenyl)chroman-2-carboxamide (SUL-104); 6-hydroxy-2,5,7,8-tetramethyl-N-(3-nitrophenyl)chroman-2-carboxamide (SUL-105); N-(4-fluorophenyl)-6-hydroxy-2,5,7,8-tetramethylchroman-2-carboxamide (SUL-106); methyl 4-(6-hydroxy-2,5,7,8-tetramethylchroman-2-carboxamido)benzoate (SUL-107); N—((R)-2-amino-2-oxo-1-phenylethyl)-6-hydroxy-2,5,7,8-tetramethylchroman-2-carboxamide (SUL-111); (6-hydroxy-2,5,7,8-tetramethylchroman-2-yl)((S)-2-(hydroxymethyl)pyrrolidin-1-yl)methanone (SUL-112); 2-(((4-fluorobenzyl)amino)methyl)-2,5,7,8-tetramethylchroman-6-ol (SUL-116); 2-(((S)-2-(hydroxymethyl)pyrrolidin-1-yl) methyl)-2,5,7,8-tetramethylchroman-6-ol (SUL-128); 2-((((S)-2-hydroxy-1-phenylethyl)amino)methyl)-2,5,7,8-tetramethylchroman-6-ol (SUL-129); 2-(((S)-2-(hydroxymethyl)pyrrolidin-1-yl)methyl)-2,5,7,8-tetramethylchroman-6-ol (SUL-134); 2-4(R-2-(hydroxymethyl)pyrrolidin-1-yl) methyl)-2,5,7,8-tetramethylchroman-6-ol (SUL135); (6-hydroxy-5, 7-diisopropyl-2,8-dimethylchroman-2-yl) (piperazin-1-yl)methanone (SUL-137); 1-(6-hydroxy-2,5,7,8-tetramethylchroman-2-carbonyl)-pyrrolidine-S-2-carboxylic acid (SUL-143) and pharmaceutically acceptable salts thereof.

In a preferred embodiment, the chromanol compound is chosen from the group consisting of the 2R enantiomer of (6-hydroxy-2,5,7,8-tetramethylchroman-2-yl)(piperazin-1-yl)methanone; N-(benzyl)-6-hydroxy-2,5,7,8-tetramethylchroman-2-carboxamide; -N-(phenyl)-6-hydroxy-2,5,7,8-tetramethylchroman-2-carboxamide; methyl 4-(6-hydroxy-2,5,7,8-tetramethylchroman-2-carboxamido)benzoate; and pharmaceutically acceptable salts thereof.

In another particularly preferred embodiment, the chromanol compound is chosen from the group consisting of the 2R enantiomer of (6-hydroxy-2,5,7,8-tetramethylchroman-2-yl)(morpholino)methanone, and (6-hydroxy-2,5,7,8-tetramethylchroman-2-yl)(piperazin-1-yl)methanone.

According to a most preferred embodiment, the present invention relates to the (R) enantiomeric form of a 6-chromanol derivative, wherein said 6-chromanol derivative is (R)(6-hydroxy-2,5,7,8-tetramethylchroman-2-yl)(piperazin-1-yl)methanone and pharmaceutically acceptable salts thereof.

According to yet another preferred embodiment, the present invention relates to the (R) enantiomeric form of a 6-chromanol derivative as described, wherein the vasoconstriction related disorder is selected from the group consisting of pulmonary hypertension, portal hypertension, vasospastic diseases, Raynaud's disease, acrocyanosis, livedo reticularis, post-traumatic dystrophy, occlusive diseases associated with inflammation, (pre)eclampsia, and Buerger's disease. Pulmonary hypertension in particular relates to pulmonary arterial hypertension, for which the present invention is preferred. Another disorder that can be treated with the described compounds is cardiac hypertrophy and fibrosis.

The vasoconstriction disorder particularly relates to α1 adrenoceptor mediated disorders, such as pulmonary arterial hypertension and cardiac hypertrophy and fibrosis.

Another indication which is preferably treated with the compounds of the present invention is heart failure with preserved ejection fraction (HFpEF), in which hypertension generally is co-indicated.

In a preferred embodiment, the vasoconstrictive disorder has a co-indication of inflammation. As the chromanol compounds are effective as anti-inflammatory agents, the use of said chromanol compounds is very effective in the prophylaxis or treatment of vasoconstrictive and inflammation related disorders, such as pulmonary hypertension, portal hypertension and (pre)eclampsia.

SUL-121 is a 1:1 racemic mixture of two enantiomers (S enantiomer named SUL-151, R enantiomer named SUL-150). The effects of SUL-150 and SUL-151 on phenylephrine (PE)-induced vascular constrictions were investigated. The results showed that whereas SUL-150 exerted a dose-dependent increase of EC50, whereas no significant effects after treatment with SUL-151 were observed. The SUL-150 was able to inhibit or counteract the induced vascular constrictions.

According to a preferred embodiment, the present invention relates to the (R) enantiomeric form of a 6-chromanol derivative, wherein said prophylaxis or treatment of vasoconstriction related disorders or conditions is mediated by inhibition of the α1 adrenoceptor. $\alpha_1$ adrenoceptors are coupled with the G-protein (GPRC), specifically $G_q$ and $G_{11}$ subtypes. Their activation leads to a downstream activation of phospholipase pathways, increase of ($Ca^{2+}$), and a subsequent constriction of the vascular smooth muscle. Additionally, we have demonstrated the ability of $\alpha_1$ adrenoceptors to trans-activate the Epidermal Growth Factor Receptor (EGFR) which contributes to downstream phosphorylation of extracellular signal-regulated kinases 1 and 2. The inhibition of EGFR attenuated constriction responses to PE in isolated rat aortas. Therefore, we investigate the effects of SUL-150 on the mechanism of EGFR transactivation by α1 adrenoceptors.

It was found that the mechanism through which SUL-150 inhibits vasoconstriction is via direct interaction with the $\alpha_1$ adrenoceptor as a receptor antagonist. SUL-151 did not affect calcium transients in any of the investigated α1 adrenoceptor subtypes. Results indicate that SUL-150 is capable of counteracting vascular constriction and intracellular calcium responses specifically via its action on $\alpha_1$ adrenoceptors. Radiolabelled prazosin displacement suggests that SUL-150 competitively binds to the antagonist binding site. Prazosin is an $\alpha_1$-blocker which acts as an inverse agonist at alpha-1 adrenergic receptors. Compared with prazosin, SUL-150 conveys a range of additional beneficial effects. Combined anti-oxidant, anti-inflammatory and vasodilatory properties of SUL-150 may be applicable in the treatment of diseases related to vasoconstriction, such as Raynaud's disease.

The present invention, according to a further aspect, relates to (R)(6-hydroxy-2,5,7,8-tetramethylchroman-2-yl)(piperazin-1-yl)methanone, and to the use of said compound and pharmaceutically acceptable salts thereof as a medicament.

According to preferred embodiment, the present invention relates to the 2R-6-chromanol derivative, wherein the prophylaxis or treatment of vasoconstriction related disorders or conditions is mediated by inhibition of the α1 adrenoceptor.

The compounds are preferably used in effective amounts, to achieve a vasodilatory effect. Effects are observed with amounts of 1 μM, but preferably higher amounts are used. Preferred amounts are concentrations in vivo or in vitro of about 10 μM or higher, more preferably about 20 μM or higher. Generally, a concentration in human of about 200 μM or lower should be sufficient and safe.

For human use, this would mean—assuming a 30 L distribution volume, 100% availability and a concentration of about 1 μM—a dosage of about 10 mg or more. Preferred amounts would result in a concentration of about 10 μM—for which a dosage of about 100 mg or more would be suitable. Hence, preferably, dosage forms of about 20 mg or more, preferably 50 mg or more, preferably 100 mg or more are suitable. Generally, solid, oral dosage forms contain as a maximum about 500 mg compound, preferably about 450 mg or less, to allow for excipients. With i.v. other liquid forms of administration, larger amounts can be administered.

Examples of dosages which can be used are an effective amount of the compounds of the invention of a dosage of 0.2 mg/kg or higher, such as preferably within the range of about 1 mg/kg to about 100 mg/kg, or within about 2 mg/kg to about 40 mg/kg body weight, or within about 3 mg/kg to about 30 mg/kg body weight, or within about 4 mg/kg to about 15 mg/kg body weight. Compounds of the present invention may be administered in a single daily dose, or the total daily dosage may be administered in divided dosage of two, three or four times daily.

The compounds described herein can be formulated as pharmaceutical compositions by formulation with additives such as pharmaceutically or physiologically acceptable excipients carriers, and vehicles. Suitable pharmaceutically or physiologically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21" edition (2005).

A pharmaceutical composition can comprise a unit dose formulation, where the unit dose is a dose sufficient to have an vasodilatory effect, preferably a vasodilatory therapeutic effect. The unit dose may be a dose administered periodically in a course of treatment or suppression of a vasodilatory disorder.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly (phosphoesters), poly amides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically or physiologically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration.

Oral administration is a preferred route of administration, and formulations suitable for oral administration are preferred formulations.

The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The invention also provides articles of manufacture and kits containing materials useful for treating, preventing, or suppressing symptoms associated with vasodilatory related conditions or disorders. The article of manufacture comprises a container with a label. Suitable containers include, for example, bottles, vials, and test tubes. The containers may be formed from a variety of materials such as glass or plastic. The container holds a composition having an active agent which is effective for treating, preventing, or suppressing symptoms associated with a vasodilatory disorder or with a condition associated with vasodilatory dysfunction. The active agent in the composition is one or more of the compounds of the invention. The label on the container preferably indicates that the composition is used for treating, preventing, or suppressing symptoms associated with a vasodilatory related disorder or condition, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy or condition to be treated. The unit dosage chosen is usually fabricated and administered to provide a defined final concentration of drug in the blood, tissues, organs, or other targeted region of the body. The effective amount for a given situation can be readily determined by routine experimentation and is within the skill and judgment of the ordinary clinician or skilled person.

The present invention will be further illustrated using the examples below. In the examples, reference is made to figures wherein FIG. 1: Shows the constriction responses to phenylephrine (PE) in the presence of different doses of SUL-150 (B) and SUL-151 (C). Methoxamine-induced vasoconstriction was measured with intact endothelium (D) and endothelium-denuded rings (E) in the presence of vehicle (0.1% DMSO) and two dosages (30 µM and 100 µM) of SUL-150. Data is obtained from 2-3 experiments (n=4-6 per group). Constriction in FIGS. 1B and 1C is expressed as percentage of response to final PE addition.

Figure 2:
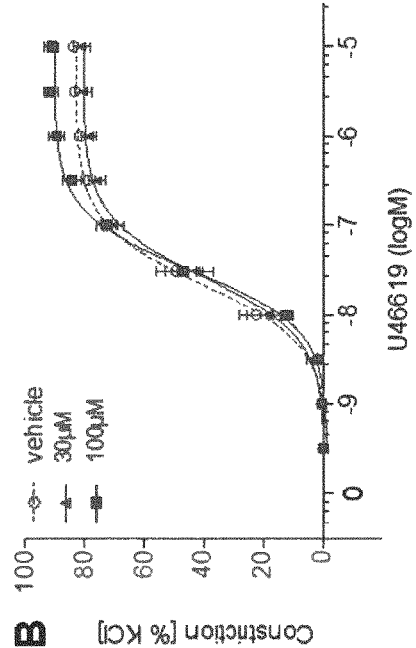
Figure 2:
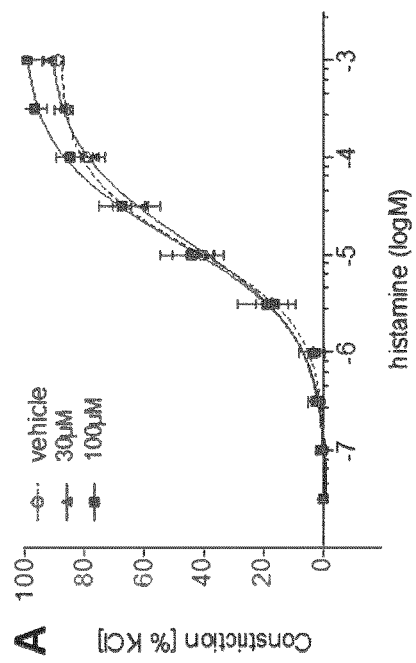

FIG. 2: Shows constriction responses to histamine (A) and the thromboxane agonist U46619 (B) after pre-treatment with vehicle (0.1% DMSO) and two dosages (30 µM and 100 µM) of SUL-150.

Figure 3:
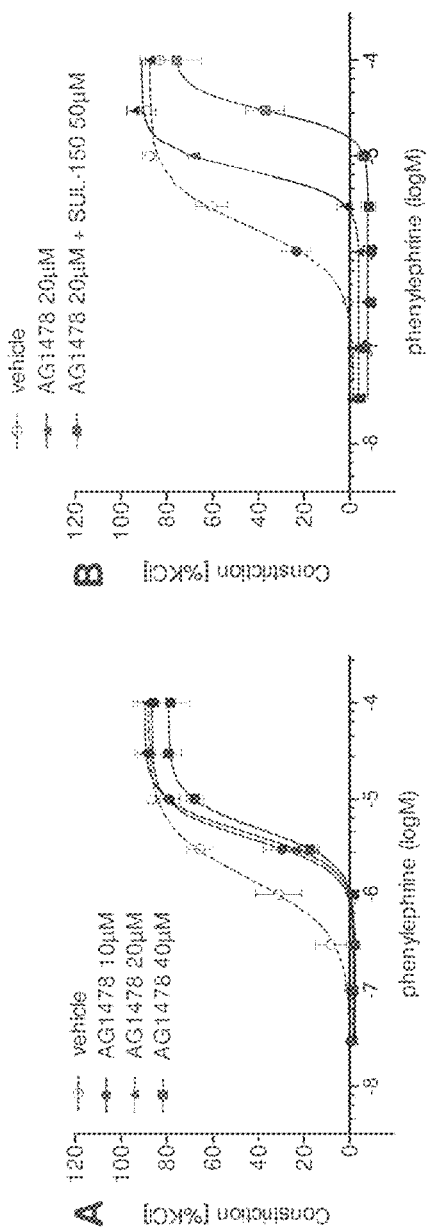

FIG. 3: Shows constriction responses to phenylephrine in the presence of vehicle and three concentrations of the EGFR inhibitor AG1478 (A) and 20 µM AG1478 with 50 µM SUL-150 (B).

Figure 4:
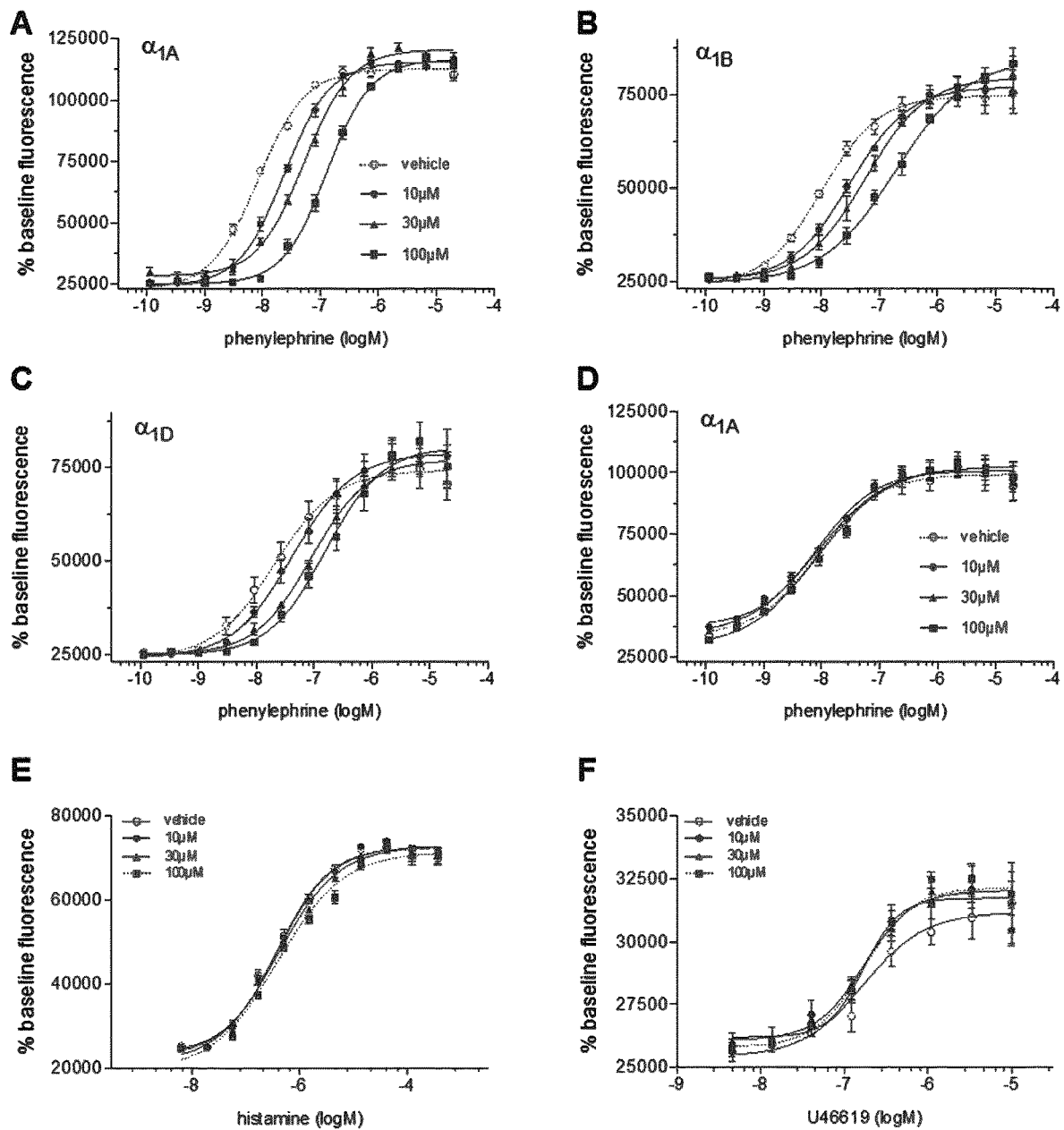

FIG. 4: Shows intracellular calcium measurements in transgenic CHO cells overexpressing $\alpha_1$ adrenoceptor subtypes A (A), B (B) and D (C) after stimulation with phenylephrine in the presence of vehicle (10% DMSO), 10 µM, 30 µM or 100 µM SUL-150. Figure D shows the lack of effect of SUL-151. Figures E and F show intracellular calcium transients mediated by histamine and U46619, respectively, in HeLa cells after treatment with SUL-150.

Figure 5:
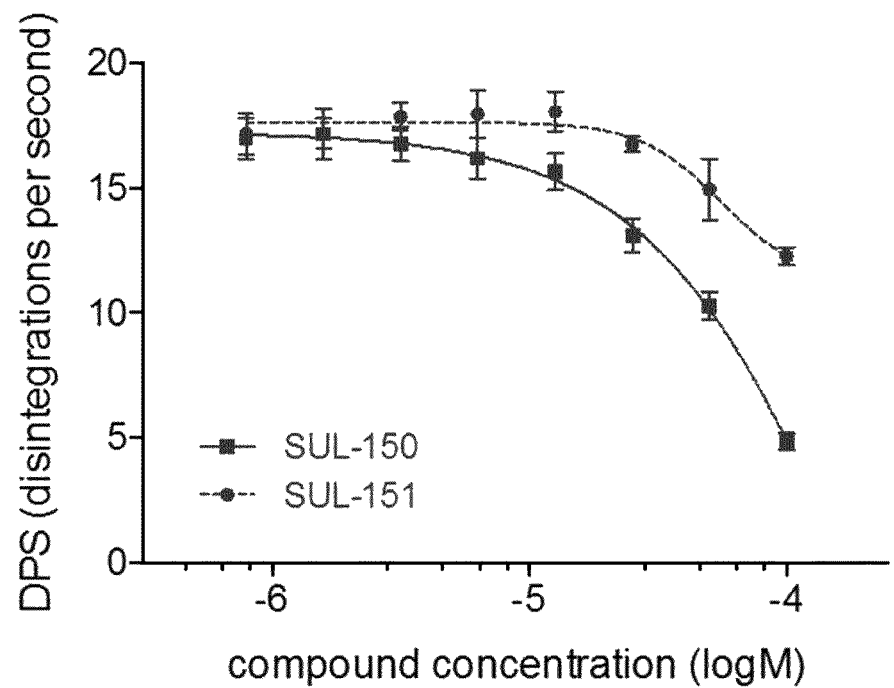

FIG. 5: Shows displacement of tritium-labelled prazosin by SUL-150 and SUL-151 in $\alpha_{1A}$ adrenoceptor transgenic CHO cells.

Figure 6:
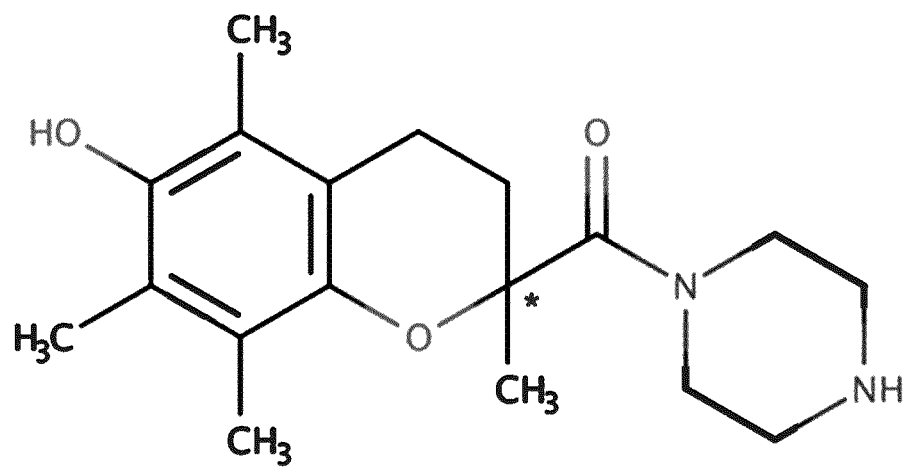

FIG. 6: Shows the structural formula of the SUL-121 ((6-hydroxy-2,5,7,8-tetramethylchroman-2-yl)-(piperaziniyl)-methanone) compound. SUL-121 is a racemic 1:1 mixture of (R)-enantiomer SUL-150 and (S)-enantiomer SUL-151. The * indicates the chiral centre of SUL-121 in the structural formula, which is at the 2 position in the chromanol group. Therefore, generally, the group of enantiomers is named the "2-R enantiomer of".

EXAMPLES

Example 1

Tissue Preparation and Myography in Isolated Porcine Renal Arteries

Porcine kidneys were obtained from a local slaughterhouse (Kroon Vlees, Gotenburgweg 30, 9723 TM Groningen. The Netherlands) and transported on ice in normal physiological Krebs buffer containing 120 mM NaCl, 6 mM KCl, 2.5 mM $CaCl_2 \times 2H_2O$, 1.2 mM $MgCl_2 \times 6H_2O$, 1.2 mM $NaH_2PO_4 \times H_2O$, 25 mM $NaHCO_3$ and 11.4 mM D-(+)-Glucose monohydrate (all ingredients were purchased from Merck) in ultrapure water.

The renal artery tree was dissected from the kidney, cleaned of surrounding connective tissue and cut into equally-sized ring segments (2 mm in length). In some rings, endothelium denudation was performed by gentle rubbing of the intimal surface with a paper clip. Rings were mounted in organ baths as described previously (Buikema et al., 2000). Arterial rings were washed thoroughly by replacing Krebs buffer and allowed to equilibrate for a period of 60 min under 1.4 g of resting tension before they were assessed for viability by inducing 2 subsequent constrictions with KCl (60 mM). Rings that failed to produce a threshold increase in diameter of 100 µm were excluded. After washout and stabilization, rings were treated for 30 minutes by incubation with vehicle (0.1% DMSO), SUL-121, SUL-150 or SUL-151, followed by subsequent incubation with cumulative doses of phenylephrine.

Dose-dependent constriction responses to phenylephrine ($10^{-8}M$-$10^{-4}M$) were recorded in said isolated porcine intrarenal arteries. Buffer was warmed to 37° C. and aerated with 95% $O_2$ and 5% $CO_2$ before use.

Example 2

Cell Culture

CHO-K1 cells were stably transfected with a plasmid containing human a1-AR subtypes A, B and D in separate cell lines in DMEM-F12 medium with 10% FBS, 1% penicillin-streptomycin and 200 µg/mL Geneticin (G418, Invitrogen, Carlsbad, CA).

HeLa cells endogenously expressing histamine and TP receptors were grown in DMEM-F12 medium enriched with 10% FBS and 1% penicillin-streptomycin. Cells were kept in a tissue culture incubator at 37° C. in 5% $O_2$/95% $CO_2$ atmosphere and grown in 75 $cm^2$ non-treated cell culture flasks. Plating was performed 24 hours before measurement on black transparent-bottom 96-well plates at 20,000 cells per well density.

Example 3

Intracellular Calcium Assays

On the next day, CHO cells were treated with either vehicle (0.1% DMSO) or SUL-121 enantiomers for 30 min at 37° C. and stimulated with a 3-fold dilution series of PE (20 µM-100 pM). $[Ca^2]_i$ was measured using the fluorescent FLIPR Calcium 6 assay kit (Molecular Devices) in immortalized CHO cells stably expressing the $\alpha_1$ adrenoceptor.

Initially, calcium responses induced by non-cumulative concentration series of phenylephrine were investigated using fluorescent measurements in $\alpha_{1A}$ adrenoceptor-overexpressing CHO cells treated with SUL-150 and SUL-151 (FIG. 4). Fluorescent measurement data was processed and analyzed in SoftMax Pro 7 and expressed as % of baseline AUC with a 3-fold multiplier using an average of first 10 measurement points as baseline.

The "Vehicle" used in all experiments is 0.1% DMSO solution.

Data and Statistical Analysis

Vascular constriction responses are expressed as percentage of final response to KCl. Data are expressed as mean±SEM. *$p<0.05$.

Example 4

Induced Fit Molecular Docking Simulation

The binding of SUL-150 to the antagonist binding site on the $\alpha_{1A}$-AR, induced fit molecular docking simulation was performed, using prazosin as a reference as follows.

The primary sequence of $\alpha_{1A}$ adrenoceptor was obtained from UniProt database (The UniProt Consortium, 2017) using reference code P35348 and uploaded to SWISS-MODEL in order to build a homology model, resulting in 373 templates. Subsequently, template ligand codes were used to query the PDB database to obtain structural data in SMILES format, which were processed by Chemmine to detect similarities with SUL-150. The SWISS-MODEL template that contained a ligand with the highest similarity score (a D3 dopamine receptor in complex with, Eticlopride, ETQ) was used to align the $\alpha_{1A}$-AR sequence onto a modelled backbone. The resulting homology model was validated by Ramachandran plot and prepared with Protein Preparation Wizard by the addition of hydrogens, bond order assignment, generation of partial charges to heteroatoms and disulfide bonds. Final refinement was performed by hydrogen bond assignment at pH 7.4 and restrained minimization at 0.3 RMSD.

Prazosin, SUL-150 and SUL-151 structural files were converted from SMILES to 3D structures using LigPrep. Protonation states were generated with Epik at pH 7.4 and small molecule energy parameters were computed using OPLS3 forcefield.

Flexible molecular docking simulation was performed using Induced Fit, part of the Schrödinger Small-Molecule Drug Discovery suite. A binding centroid was defined between residues involved in antagonist binding confirmed by mutagenesis (PHE312, PHE308 and ASP106) and ligands were docked within 15 Å, using an extended sampling protocol without constrains. Residues within 5 Å of resulting ligand poses were refined using Prime to improve ligand conformational sampling. Finally, the Scorpion server was used for the assessment and classification of small molecule-protein interactions and the final results were rendered using PyMOL 2.0.

Results

Effects of SUL-150 and SUL-151 on $\alpha_1$ Adrenoceptor Mediated Vasoconstriction To explore the effects of the enantiomers of (6-hydroxy-2,5,7,8-tetramethylchroman-2-yl)(piperazin-1-yl)methanone (SUL-150 and SUL-151) on constriction of isolated porcine intrarenal arteries, cumulative dose response curves to the $\alpha_1$ adrenoceptor agonist phenylephrine (PE) were constructed in the presence and absence of SUL-150 and SUL-151. The results are presented in Table 1.

TABLE 1

LogEC$_{50}$ values of phenylephrine-induced constriction responses in the presence of SUL-150 and SUL-151.

| logEC$_{50}$ | Phenylephrine | |
|---|---|---|
| | SUL-150 | SUL-151 |
| Vehicle | −5.77 ± 0.04 | |
| 10 μM | −5.11 ± 0.09* | −5.82 ± 0.05 |
| 30 μM | −5.06 ± 0.06* | −5.89 ± 0.04# |
| 100 μM | −4.44 ± 0.09* | −5.77 ± 0.04 | p < 0.05 vs vehicle
*p < 0.0001 vs vehicle

Whereas SUL-150 exerted a dose-dependent increase of EC$_{50}$ (FIG. 1A, Table 1), we observed no significant effects after treatment with SUL-151 (FIG. 1B, Table 1).

Additionally, the effects of SUL-150 were investigated on stimulation with methoxamine, which is an alternative $\alpha_1$ adrenoceptor agonist. Similar to PE, dose response curves to methoxamine were shifted rightward by SUL-150 pre-treatment (FIG. 1C). Removal of the endothelium did not abrogate the effects of SUL-150 on methoxamine induced constriction (FIG. 1D).

Effects of SUL-150 on Histamine and U46619 Induced Vasoconstriction

To gain insight into receptor specificity of SUL-150, the effects of SUL-150 on histamine and U46619 (a synthetic thromboxane agonist) induced constrictions were investigated (FIG. 2). SUL-150 did not affect constriction responses to histamine (Table 2) and although the shift in EC50 of U46619-induced constrictions in the presence of 100 μM SUL-150 was statistically significant (Table 2), the small effect size led us to exclude an action of SUL-150 on thromboxane receptors.

TABLE 2

LogEC$_{50}$ values of histamine and U46619-induced constriction responses in the presence of SUL-150.

| | histamine | | U46619 | |
|---|---|---|---|---|
| logEC$_{50}$ | Porcine renalis | HeLa cells | Porcine renalis | HeLa cells |
| Vehicle | −4.94 ± 0.03 | −6.47 ± 0.05 | −7.65 ± 0.05 | −6.62 ± 0.18 |
| 10 μM | | −6.45 ± 0.05 | | −6.83 ± 0.10 |
| 30 μM | −4.86 ± 0.08 | −6.39 ± 0.05 | −7.58 ± 0.06 | −6.78 ± 0.18 |
| 100 μM | −4.85 ± 0.10 | −6.29 ± 0.06* | −7.50 ± 0.04* | −6.75 ± 0.10 |

*p < 0.05 versus vehicle

Effects of SUL-150 Mediated Through EGFR Transactivation

Inhibition of EGF receptor (EGFR) transactivation is known to inhibit $\alpha_1$ adrenoceptor mediated constrictions (REF). Therefore, we investigated the role of EGFR transactivation in SUL-150 mediated inhibition of vasoconstriction. For this, porcine intrarenal arteries were pre-treated with the EGFR blocker AG1478 (FIG. 3). First, an initial measurement was performed to determine the dose of AG1478 which would cause maximal inhibition of vascular constriction induced by PE (FIG. 3A). Subsequently, isolated arteries were treated with AG1478 (20 μM) and SUL-150 (50 μM) and studied for PE-induced vasoconstriction. Despite maximal inhibition of EGFR transactivation by AG1478, SUL-150 still demonstrated an additional inhibitory effect on PE-mediated constriction (FIG. 3B).

Effects of SUL-150 on PE-Induced Intracellular Calcium Signalling

To further investigate the mechanisms through which SUL-150 inhibits $\alpha_1$ adrenoceptor mediated contractions, PE-induced calcium transients were studied in CHO cells stably overexpressing the human $\alpha_1$ adrenoceptor subtypes A, B and D. SUL-150 shifted dose response curves rightwards for all three $\alpha_1$ adrenoceptor subtypes (FIGS. 4A, B and C, Table 3). SUL-151 did not affect calcium transients in any of the investigated $\alpha_1$ adrenoceptor subtypes (only shown for the $\alpha_1$ adrenoceptor A subtype in FIG. 4D).

TABLE 3

LogEC$_{50}$ values of phenylephrine-induced calcium
influx after treatment with SUL-150.

| logEC$_{50}$ | SUL-150 | | | SUL-151 |
| --- | --- | --- | --- | --- |
| | α$_{1A}$ | α$_{1B}$ | α$_{1D}$ | α$_{1A}$ |
| Vehicle | −8.07 ± 0.03 | −7.99 ± 0.08 | −7.68 ± 0.13 | −8.10 ± 0.11 |
| 10 μM | −7.62 ± 0.03* | −7.51 ± 0.08* | −7.37 ± 0.10 | −8.09 ± 0.10 |
| 30 μM | −7.28 ± 0.03* | −7.24 ± 0.07* | −7.04 ± 0.06* | −8.09 ± 0.11 |
| 100 μM | −6.88 ± 0.03* | −6.72 ± 0.08* | −6.80 ± 0.10* | −7.98 ± 0.10 |

*p < 0.0001 versus vehicle

Effects of SUL-150 on Histamine- and U46619-Induced Intracellular Calcium Signalling To confirm specificity of SUL-150 for the α$_1$ adrenoceptor additionally histamine and U46619 induced calcium transients were studied in HeLa cells endogenously expressing human histamine H$_1$ receptor. SUL-150 did not significantly affect histamine and U46619 induced calcium transients (FIGS. 4E, 4F and Table 2).

Radioligand Binding Assay in α$_{1A}$ Adrenoceptor Overexpressing CHO Cells

SUL-150 affected PE-induced calcium transients, indicating that the effects of SUL-150 are upstream of calcium. We therefore explored whether SUL-150 could directly interact with the α$_1$ adrenoceptor as a receptor antagonist. For this, a displacement binding assay was performed on the α$_{1A}$ adrenoceptor transgenic CHO cells using radiolabeled prazosin, an established α$_{1A}$ adrenoceptor antagonist. SUL-150 was more potent in displacing the radioligand compared to SUL-151, which displaced [7-Methoxy-3H]-prazosin only at concentrations higher than 10 μM (FIG. 5).

Induced Fit Molecular Modelling

Prazosin coexists in two protonation forms at pH 7.4. In the protonated form, the N1 assumes a positive charge, subsequently forming a salt bridge with the negatively charged side chain of ASP106, ultimately causing this form to assume an inverted orientation relative to its non-protonated form. The quinazoline scaffold of non-protonated prazosin was docked close to TM5 to form a confocal hydrogen bond between the 6,7-methoxy groups and SER188, a hydrogen bond between furan oxygen and SER83, and between prazosin carboxamide and GLN177 side chain; van der Waals interactions with side chains of PHE86, VAL107, ILE178, PHE289, MET292, and PHE312; π-π interactions with PHE288 and PHE312; and a π-hydrogen bond interaction with the side chain carboxy group and backbone peptide carboxamide of ASP106. The proposed binding mode of non-protonated prazosin indicated interactions which were in accord with those described in the literature.

An induced fit of SUL-150 and SUL-151 demonstrated alignment of the chromane scaffold with prazosin quinazoline, 6-hydroxy groups (SUL) and 6-metoxy (prazosin) as well as over their common piperazine moiety. Residues which were involved in forming contacts with all three compounds were VAL107, ILE178, SER188, PHE288, PHE289.

Glide scores computed using the Schrödinger Small-Drug Discovery Suite were −10.8 kcal×mol$^{-1}$, −10.2 kcal×mol and −9.4 kcal×mol$^{-1}$ for prazosin, SUL-150 and SUL-151 respectively. Prazosin and SUL-150 formed contacts with PHE312 and ASP106 confirmed in prazosin binding by mutagenesis, whereas SUL-151 did not show interactions with these residues. Additionally, the chirality of SUL-150 enables the orientation of its carboxamide towards ASN179, effectively forming a hydrogen bond. Additional hydrogen bond was formed between its protonated N-terminal and TYR316.

Comparison of the binding site-interactions of the several SUL compounds with the binding SUL-150, and the non-binding of SUL-151 and SUL-132 and SUL-138, allowed the prediction that the now claimed SUL-compounds indeed have the binding properties claimed.

The invention claimed is:

1. Method of treatment or prophylaxis of vasoconstriction related disorders or conditions, comprising administering a (2R) enantiomeric form of a 6-chromanol derivative wherein said 6-chromanol derivative is (6-hydroxy-2,5,7,8-tetramethylchroman-2-yl) (piperazin-1-yl) methanone and pharmaceutically acceptable salts thereof,
wherein said vasoconstriction related disorder is selected from the group consisting of heart failure with preserved ejection fraction and cardiac hypertrophy, fibrosis, pulmonary hypertension, portal hypertension, vasospastic diseases, Raynaud's disease, acrocyanosis, livedo reticularis, post-traumatic dystrophy, occlusive diseases associated with inflammation, (pre) eclampsia, and Buerger's disease.

2. The method of treatment or prophylaxis of vasoconstriction related disorders or conditions according to claim 1, wherein said prophylaxis or treatment of vasoconstriction related disorders or conditions is mediated by inhibition of the a1 adrenoceptor.

3. The method of treatment or prophylaxis of vasoconstriction related disorders or conditions according to claim 2, wherein said prophylaxis or treatment of vasoconstriction related disorders or conditions is pulmonary arterial hypertension.

4. The method of treatment or prophylaxis of vasoconstriction related disorders or conditions according to claim 1, wherein the 6-chromanol derivative is administered in an amount sufficient to achieve a concentration of 1 μM or higher.

5. The method of treatment or prophylaxis of vasoconstriction related disorders or conditions according to claim 2, wherein the 6-chromanol derivative compound is administered in an amount sufficient to achieve a concentration of about 10 μM or higher.

6. The method of treatment or prophylaxis of vasoconstriction related disorders or conditions according to claim 1, wherein the 6-chromanol derivative is formulated as a pharmaceutical dosage form wherein said 6-chromanol derivative is present in an amount of 10 mg-500 mg.

7. The method of treatment or prophylaxis of vasoconstriction related disorders or conditions according to claim 1, wherein the dosage form is a solid dosage form.

8. The method of treatment or prophylaxis of vasoconstriction related disorders or conditions according to claim 6, wherein said 6-chromanol derivative is present in an amount of 100-500 mg.

9. The method of treatment or prophylaxis of vasoconstriction related disorders or conditions according to claim 7, wherein the dosage form is a solid oral dosage form.

10. The method of treatment or prophylaxis of vasoconstriction related disorders or conditions according to claim 2, wherein said prophylaxis or treatment of vasoconstriction related disorders or conditions is heart failure with preserved ejection fraction.

* * * * *